United States Patent
Gibby et al.

[11] Patent Number: 5,804,163
[45] Date of Patent: *Sep. 8, 1998

[54] CONTRAST AGENTS FOR MAGNETIC RESONANCE IMAGING AMINOSACCHARIDE

[75] Inventors: Wendell A. Gibby, Mapleton; N. Rao Puttagunta, Provo, both of Utah

[73] Assignee: Magnetic Research, Inc., Provo, Utah

[*] Notice: The term of this patent shall not extend beyond the expiration date of Pat. No. 5,330,745.

[21] Appl. No.: 274,966

[22] Filed: Jul. 14, 1994

Related U.S. Application Data

[62] Division of Ser. No. 975,607, Nov. 12, 1992, Pat. No. 5,330,743.

[51] Int. Cl.$^6$ .................................................. A61B 5/055
[52] U.S. Cl. .............. 424/936.1; 424/9.35; 424/9.364; 534/16; 514/184; 514/836; 556/50; 556/55; 556/63; 556/77; 556/105; 556/116; 556/134; 556/148
[58] Field of Search ............... 424/9.361, 9.35, 424/9.364; 128/653.4, 654; 436/173; 534/16; 514/184, 836; 556/50, 55, 63, 77, 105, 116, 134, 148; 536/29.1

[56] References Cited

U.S. PATENT DOCUMENTS

| | | | |
|---|---|---|---|
| 4,863,716 | 9/1989 | Quay et al. | 424/9.361 |
| 4,880,008 | 11/1989 | Lauffer | 128/654 |
| 4,935,518 | 6/1990 | Rocklage et al. | 546/6 |
| 5,011,925 | 4/1991 | Rajagopalan | 544/58.1 |
| 5,023,072 | 6/1991 | Cheng | 424/9 |
| 5,057,302 | 10/1991 | Johnson et al. | 424/101 |
| 5,077,037 | 12/1991 | Wallace | 424/9 |
| 5,138,040 | 8/1992 | Moore et al. | 534/16 |
| 5,155,215 | 10/1992 | Ranney | 534/16 |
| 5,250,285 | 10/1993 | Lauffer et al. | 424/9.361 |
| 5,290,537 | 3/1994 | Moore et al. | 424/9 |
| 5,312,617 | 5/1994 | Unger et al. | 424/9 |
| 5,330,743 | 7/1994 | Gibby | 424/9.35 |
| 5,399,340 | 3/1995 | Radüchel et al. | 424/9.361 |
| 5,403,576 | 4/1995 | Lin et al. | 424/9 |

*Primary Examiner*—Gary E. Hollinden
*Attorney, Agent, or Firm*—Daniel R. Kimbell

[57] ABSTRACT

A contrast enhancing agent for magnetic resonance images having a chelating agent, which can be bound to metals having at least one unpaired electron. Examples of such chelating agents include 3,6,9-tris(carboxymethyl)-1, 11-bis(dimethylamine)-3,6,9-triazaundecane; 3,6,9-tris(carboxymethyl)-1, 11-bis(diethanolamino) 3,6,9-triazaundecane; 3,6,9-tris(carboxymethyl)-1, 11-bis(tris(hydroymethyl) aminomethane)-3,6,9-triazaundecane; 3,6-bis(carboxymethyl-1,8-bis(N-carboxymethylglucosamino)-3,6-diazoctane; DTPA-bis(galactosamide), DTPA-Bis(glucosamide), DTPA-Bis(pyridoxamide), and poly-(DTPA-ethylenediamide).

10 Claims, 2 Drawing Sheets

CONTRAST AGENTS FOR MAGNETIC RESONANCE IMAGING AMINOSACCHARIDE

This application is a division of application Ser. No. 07/975,607, filed Nov. 12, 1992, status pending.

BACKGROUND OF THE INVENTION

1. Field of the Invention

This invention relates to NMR shift reagents and in particular contrast enhancing agents for magnetic resonance imaging.

2. Brief Description of the Prior Art

Magnetic Resonance (hereinafter MR) imaging is one of the newest and least deleterious methods of viewing the interior of the human body, Radio waves interact with protons in a magnetic field to produce images having superior soft-tissue contrast compared to X-ray tomography However, the technique can be non-specific, that is, it may be impossible to distinguish from between many pathological conditions, such as between cancer and the edema surrounding the cancer, active and inactive multiple sclerosis plaques and bowel from other adjacent organs.

Contrast agents enhance various portions of the MR image by changing, usually decreasing, the relaxation times of the protons in the immediate vicinity to the agent. This allots the area of interest to be much more conspicuous than surrounding tissue One example of a contrast agent is that disclosed in the European Pat. No. 3,302,410 of A. G. Schering for gadolinium diethylene triamine pentaacetic acid complex (hereinafter Gd DTPA). Gd DATA has been attached to a variety of macromolecules, for example monoclonal antibodies, albumin, lipids and polysaccharides.

Other agents, such as ethylene diamine tetraacetic acid (hereinafter EDTA), and 1, 4, 7, 10 tetraazacyclododecane, N, N', N", N'"-tetraacetic acid (hereinafter DOTA), have been chelated with Gd in an effort to make a superior contrast agent.

The utility of a specific MRI contrast agent varies depending upon the clinical problem to be addressed and the organ of interest to be imaged. For example, extracellular fluid agents such as gadolinium DTPA, gadolinium DOTA, and gadolinium DTPA BMA (the structure of which is shown further below) work well in organs such as the brain and spinal cord, where the normal brain parenchyma has a barrier to permeability of the contrast agent and pathologic conditions such as cancer do not. However, these contrast agents work poorly for imaging of the vascular system as the majority of the material is lost to the extracellular fluid space. Furthermore, they can at times be deleterious in imaging organs such as the liver and spine in which lesions can be made to appear isointense to normal tissue. They can provoke variable enhancement patterns in organs such as the kidneys in which their high concentration first darkens and then brightens parenchyma. They are poor gut agents because of dilution effects, and poor coating of the bowel.

Some prior art chelates such as gadolinium DOTA and HP-DO3A (the structure of which is shown further below) are cyclic ring compounds which, although thermodynamically more stable than open chain compounds. However, their synthesis requires a complex, tedious, and expensive process. It would be advantageous for a compound to have improved thermodynamic stability over, say, DTPA or DTPA-BMA, yet not require the expense of ring synthesis.

It would be advantageous in certain conditions (e.g. liver metastasis) for the contrast material to specifically target organ receptors. Examples would be galactose receptors in the lever, polymeric material staying within the blood vessels and heart chambers, or intrathecal administration of a contrast agent with a glucose moiety which might attach to glucose receptors within the brain.

U.S. Pat. No. 4,933,411 to Gibby reports sugar ester derivatives of DTPA. While these are generally useful compounds, they have an unstable shelf life at neutral pH. Some prior art agents teach gadolinium DTPA BMA derivatives of DTPA with the bis-methylamide. Unfortunately, the bis-methylamide diminishes the hydrophilicity of the agent. It has been demonstrated with other X-ray contrast media that the more hydrophilic agents tend to be less toxic.

Prior art chelates of Gd, and other paramagnetic metals, suffer from several defects. The body rapidly excretes Gd DTPA, for example. Furthermore, it is not organ specific.

Another problem with known MR enhancing agents is that the proteins that are used to anchor the simple chelates, monoclonal antibodies and the like, may provoke allergic reactions in the recipient. Furthermore, proteins are expensive and carry risks of viral pathogens.

U.S. Pat. No. 4,647,447 to Gries et al. discloses a NMR diagnostic medium containing a well tolerated complex salt formed from the anion of a complexing acid and one or more. metal ions. Gries et al. discloses that the complexing acid can be conjugated with biomolecules that are known to concentrate in the organ or part of the organ to be examined. The biomolecules of Gries et al. include hormones, such as insulin; prostaglandins, steroid hormones, amino sugars, peptides, proteins and lipids. Gries et al. includes broad claims to a method of imaging body tissue in a patient by NMR tomography by administering to the patient an effective amount of a pharmaceutical agent comprising an amount, effective to affect such relaxation times, of a paramagnetic, physiologically compatible salt of a physiologically compatible chelate complex of an ion of a lanthanide element of atomic numbers 57–70, or of a transition metal of atomic numbers 21–29, 42, or 44 (claim 24 thereof) and by administering to the patient an effective amount of a pharmaceutical agent comprising an amount, effective to affect such relaxation times, of a paramagnetic, physiologically compatible salt of a complex of an ion and, as a ligand, an acyclic or cyclic complexing agent containing organic nitrogen, phosphorus, oxygen or sulfur, the complexed ion being an ion of a lanthanide element of atomic numbers 57–70, or of a transition metal of atomic numbers 21–29, 42, or 44 (claim 65). However, Gries et al. does not disclose any DTPA bisamides with aminosugars nor the specific linkages.

Patent Corporation Treaty Application No. WO 90/03804, to Cacheris, et al. discloses metal chelate compositions of DTPA-bisamides, of the formula

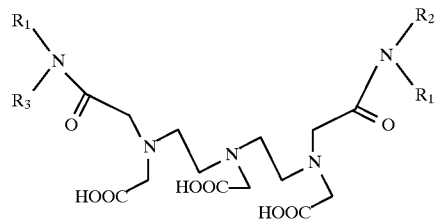

wherein $R_1$ to $R_3$ are each, independently, hydrogen, lower hydroxy (e.g. $C_{1-6}$) alkyl, hydroxy lower alkyl, or polyhydroxy ($C_{1-18}$) alkyl. Cacheris et al. nowhere discloses or suggest that $R_1$ and $R_3$ and $R_2$ may be sugars or carbohydrates. In fact, alcohols (hydroxyalkanes) are recognized as a distinctly different class of compounds from the carbohydrates. Carbohydrates are polyhydroxyaldehydes and polyhydroxyketones, not mere polyhydroxyalkanes. Due to the carbonyl functional group, carbohydrates exist as hemiacetals (cyclic structures). These same distinctions also apply to polyhydroxyalkylamines and aminosugars.

U.S. Pat. No. 5,077,037 to Wallace discloses magnetic resonance imaging agents including mono or polyhydroxy alkylamides of DTPA.

European Patent Application Publication No. 0 466 200 Alto Berg, discloses a series of aminocarboxylic acids and derivates thereof which are useful as chelating agents.

U.S. Pat. No. 5,087,440 to Cacheris, et al. discloses DTPA bisamides containing heterocyclic and hydroxyalkyl ($C_{1-6}$) amines.

It would be advantageous to have MR contrast enhancing agents that are organ specific, non-ionic and hydrophilic, do not provoke allergic reactions in the recipient, are less expensive to synthesize than cyclic compounds, yet approach the thermodynamic stability of cyclic compounds, exhibit the hydrophilic properties of sugar esters of DTPA, and retain better chemical stability.

SUMMARY OF THE INVENTION

An aspect of this invention is a composition of matter comprising a chelating agent represented by the formula:

A magnetic resonance contrast enhancing agent comprising a chelating agent representing by the formula A:

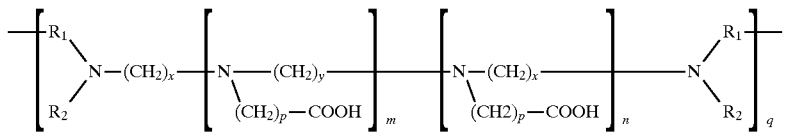

where
q=an integer from 1 to 10,000;
n=an integer between 0 and 4;
x=an integer between 1 and 4;
y=an integer between 1 and 4;
p=can be varied independently and is an integer between 0 and 2;
m=an integer between 1 and 3;
and when q=1, m=2, n=1, x=2, y=2, and p=1
$R_1$ and $R_2$ are same or different, independently, and are selected from the group consisting of H, Alkyl ($C_{1-18}$), monohydroxy or polyhydroxy alkyl ($C_{1-18}$) aryl, arylalkyl, mono or polyhydroxyaryl, substituted aryl or substituted hydroxyaryl, alkoxyalkyl, arylalkoxyalkyl, cyclohexyl, mono or polyhydroxy cyclohexyl, furfuryl, tetrahydrofurfuryl, pyranylalkyl, tetrahydropyranylalkyl, and sugar;

and when q=1, m=1, n=1, x=2, y=2, p=1

$R_1$ is selected from the group consisting of H, alkyl ($C_{1-18}$), monohydroxy or polyhydroxyalkyl ($C_{1-18}$), aryl, arylalkyl, mono or polyhydroxyaryl, substituted aryl, substituted hydroxyaryl, alkoxyalkyl, arylalkoxyalkyl, cyclohexyl, mono or polyhydroxy cyclohexyl, furfuryl, tetrahydrofurfuryl, pyranylalkyl, and tetrahydropyranylalkyl, and sugar, and $R_2$=—$CH_2$—COOH;

and when q=1, m=1, n=0, x=2, p=1

$R_1$=—$CH_2$—CO—NH—$R_3$; wherein —NH—$R_3$=is selected from the group consisting of glucosamine, galactosamine, any aminosugar, pyridoxamine, purines, pyrimidines, and nucleosides, and $R_2$=—$CH_2$—COOH; and
when q≥2, m=1, n=0, x=2, y=2, p=1,

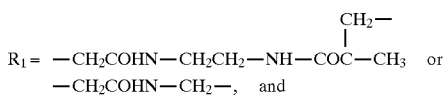

$R_2 = -CH_2-COOH$.

A further aspect of the invention is the method of use of the composition of matter recited above chelated with a paramagnetic metal ion as for enhancing the image formed by MR.

DETAILED DESCRIPTION OF THE INVENTION

Figure 1:
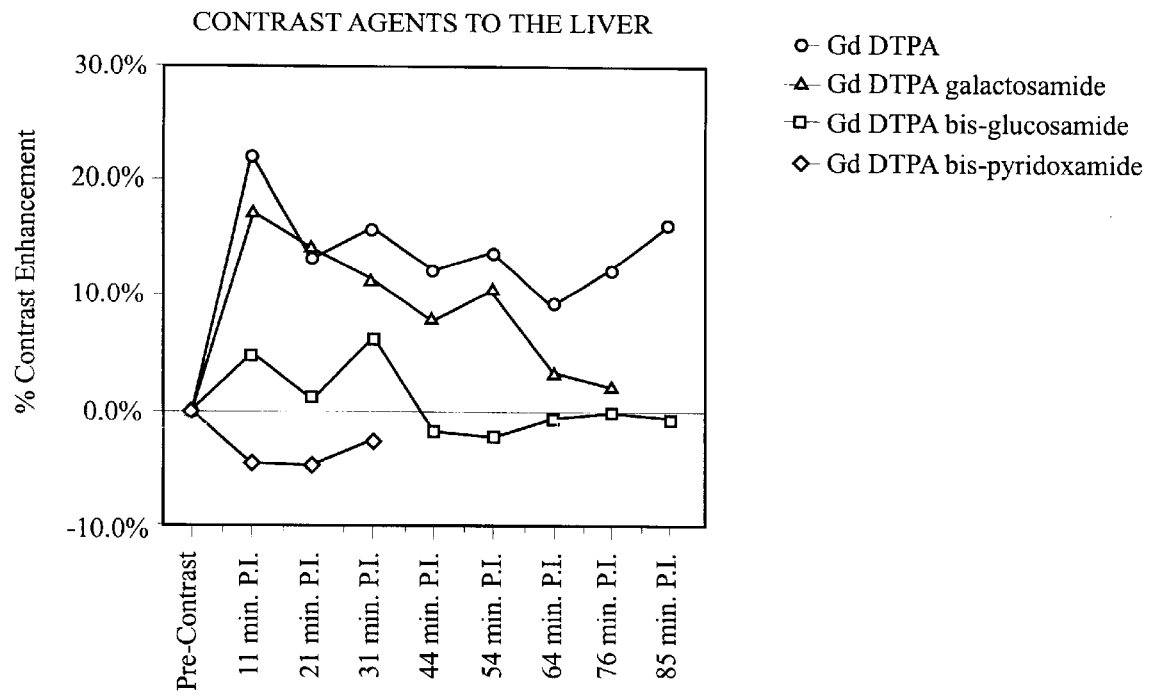
FIG. 1 is a graph of data points of contrast enhancement values in the livers of rabbits.
Figure 2:
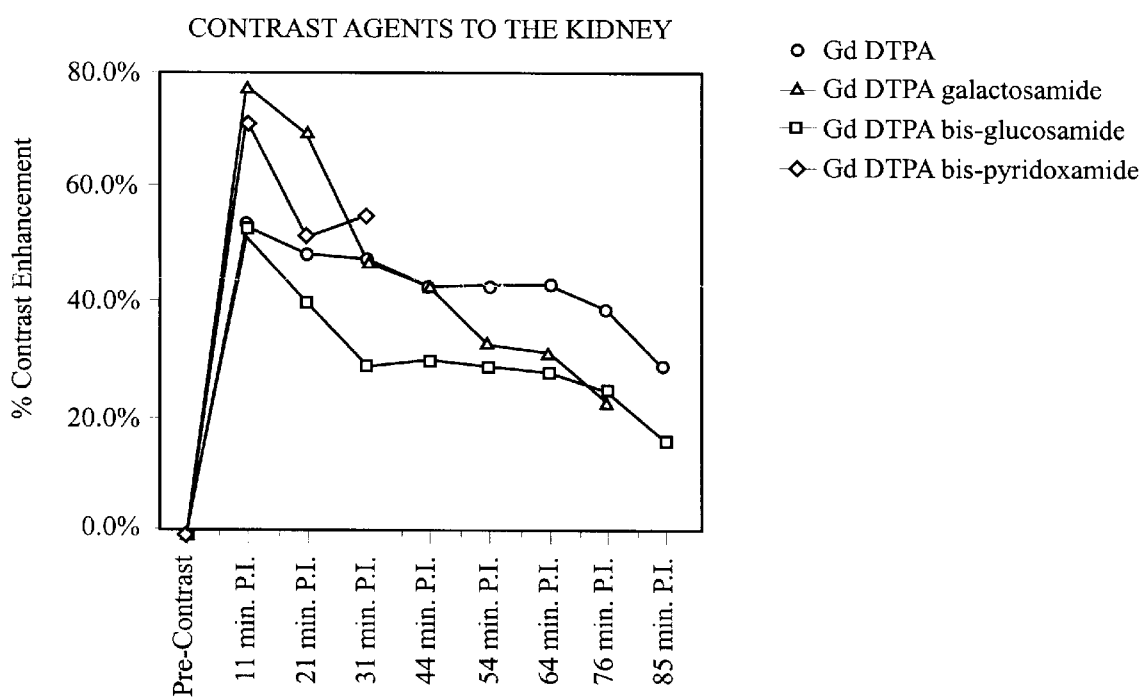
FIG. 2 is a graph of data points of contrast enhancement values in the kidneys of rabbits.
Figure 3:
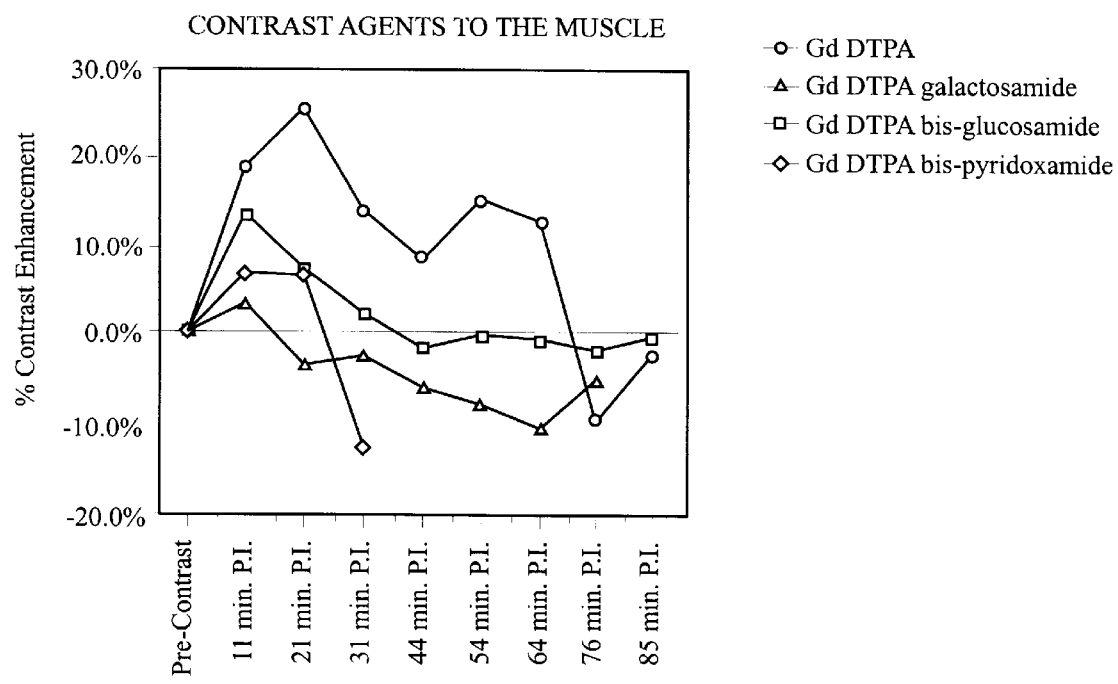
FIG. 3 is a graph of data points of contrast enhancement values in the muscles of rabbits.

The chelating agents of this invention are represented by the formula:

A magnetic resonance contrast enhancing agent comprising a chelating agent representing by the formula A:

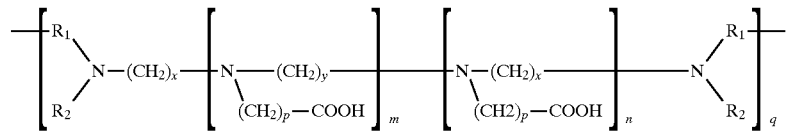

where
q=an integer from 1 to 10,000;
n=an integer between 0 and 4;
x=an integer between 1 and 4;
y an integer between 1 and 4;
p=can be varied independently and is an integer between 0 and 2;

m=an integer between 1 and 3;

and when q=1, m=2, n=1, x=2, y=2, and p=1;

$R_1$ and $R_2$ are same or different, independently, and are selected from the group consisting of H, Alkyl ($C_{1-18}$), monohydroxy or polyhydroxy alkyl ($C_{1-18}$), aryl, arylalkyl, mono or polyhydroxyaryl, substituted aryl or substitute hydroxyaryl, alkoxyalkyl, arylalkoxyalkyl, cyclohexyl, mono or polyhydroxy cyclohexyl, furfuryl, tetrahydrofurfuryl, pyranylalkyl, tetrahydropyranylalkyl, and sugar;

and when q=1, m=1, n=1, x=2, y=2, p=1

$R_1$ is selected from the group consisting of H, alkyl ($C_{1-18}$) monohydroxy or polyhydroxyalkyl ($C_{1-18}$), aryl, arylalkyl, mono or polyhydroxyaryl, substituted aryl, substituted hydroxyaryl, alkoxyalkyl, arylalkoxyalkyl, cyclohexyl, mono or polyhydroxy cyclohexyl, furfuryl, tetrahydrofurfuryl, pyranylalkyl, and tetrahydropyranylalkyl, and sugar, and $R_2 = -CH_2-COOH$;

and when q=1, m=1, n=0, x=2, y=2, p=1

$R_1 = -CH_2-CO-NH-R_3$; wherein $-NH-R_3=$ is selected from the group consisting of glucosamine, galactosamine, any aminosugar, pyridoxamine, purines, pyrimidines, or nucleosides, and $R_2 = -CH_2-COOH$; and when $q \geq 2$, m=1, n=0, x=2, y=2, p=1 ,

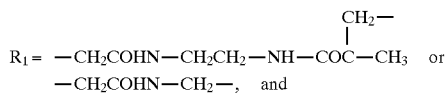

These agents tenaciously bind metal ions and can be used to place otherwise toxic metal ions in organic environments, particularly biological environments by coordinating with the metal ion and thus preventing it from poisoning critical membranes or enzymes. The toxicity of the chelate is also lessened by having a metal bound to it as it will not remove essential metals from enzymes and membranes.

Metal ions easily bind to the chelate. Preferred metal ions include those having at least one unpaired electron, which is to say, those that are paramagnetic. Examples include Cr, Mn, Fe, Co, Tc and the lanthanide metals, particularly Gd, and Dy.

The metal complexes of the chelate can then be used as contrast enhancers for MR images. The method of administration of the complex, depends on the portion of the anatomy to be imaged. For example, if the gastrointestinal tract is to be imaged, oral administration is preferred. For imaging of the liver, spleen, and kidneys, intravenous administration is preferred.

Various formulations of the metal chelate will have different physical properties. For example, highly cross linked polymeric chelate will be fairly insoluble particles, but less highly cross linked polymers are more soluble.

The clinician can use the various properties to his advantage. For example, if the area to be imaged includes delicate vascular systems, for example, the liver, or brain, a highly soluble form of metal chelate is preferred. If double contrast images of gastrointestinal tract are preferred, then more insoluble forms of metal chelate that coats the interior surface of the organs is preferred. Chelates with receptor molecules such as galactose will preferentially go to the liver.

The Gd(III) complexes of the ligands which have just three non-terminal carboxyl groups (viz. complexes in which q =1, n=1, p=an integer between 0 and 2, m=2, and $R_1$ and $R_2$ are same or different, independently, and are selected from the group consisting of H, Alkyl ($C_{1-18}$), monohydroxy or polyhydroxy alkyl ($C_{1-18}$), aryl, arylalkyl, mono or polyhydroxyaryl, substituted aryl or substituted hydroxyaryl, alkoxyalkyl, arylakoxyalkyl, cyclohexyl, mono or polyhydroxy cyclohexyl, furfuryl, tetrahydrofurfuryl, pyranylalkyl, tetrahydropyranylalkyl, and sugar, are nonionic since they have just three carboxyl groups. These non-ionic contrast agents are less osmotic, less irritating, and have lower acute toxicity compared to ionic Gd DTPA.

A prior art open chain non-ionic MR contrast agent is DTPA-BMA, (OMNISCAN), U.S. Pat. No. 4,687,659, and has the following formula:

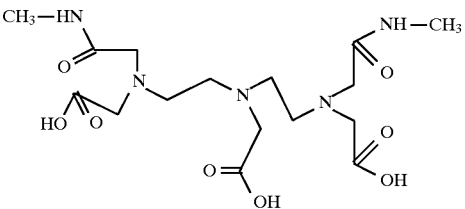

The presence of sugar and polyhydroxy groups may contribute to a lower toxity of these compounds compared with other non-ionic chelates such as Gd-DTPA-BMA. Examples of the synthesis of some of these compounds are set forth in Examples 1 through 7 which do not have amide linkage. They may also improve the thermodynamic stability with the metal ion due to metal-ligand interaction with the sugar alcohols.

Another prior art non-ionic MR contrast agents is HP-DO3A (PROHANCE), Inorganic Chemistry, 1991, 50, 1265, with the following formula:

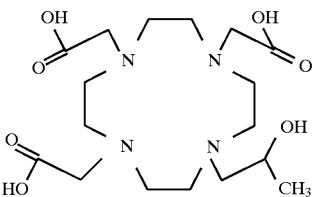

However, HPDO3A is expensive and difficult to synthesize. The more rigid ring structures improve GD-ligand stability but makes it more difficult to change groups to improve metal selectivity.

The Gd(III) complexes of the invention with two non-terminal carboxylic groups) form monoanionic complexes. These agents are less osmotic compared to dianionic agents such as Gd(III)-DTPA. Examples of the synthesis of three of these compounds are set forth in Examples 9 through 11.

The ligands wherein m=1, q=1, n=0, x=2, p=1, $R_2=-CH_2-COOH$ and $R_1=-CH_2CO-NH-R_3$, wherein $-NH-R_3=$glucosamine, galactosamine, or any aminosugar, pyridoxamine, purines, pyrimidines or nucleosides, are chemically more stable than the previous bisesters of DTPA, such as those disclosed in U.S. Pat. No. 4,822,594 to Gibby. Examples 12 and 13 disclose the synthesis of two of bisamides with aminosugars. These compounds are nonionic agents on chelation with Gd(III). Pyridoxamine is the amine form of vitamin B-6, which has receptors in the liver. DTPA bis-galactosamide may also show liver selectivity but maintains usefulness elsewhere in the body to image lesions of the brain, kidney, etc.

The polymeric compounds wherein q≥2, m=1, n=0, x=2, y=2 and p=1

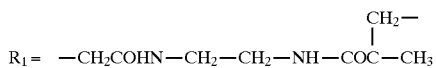

or —CH$_2$COHN—CH$_2$—as bridging groups of polymers, and R$_2$ =—CH$_2$—COOH are confined to the intravascular region when injected into the circulatory systems. These agents are more stable than polymeric agents having ester linkages, and are hydrophilic. These compounds also have good coating properties and are useful for gastrointestinal images when taken orally. Examples 13 and 14 below describe how these compounds are synthesized.

When used as magnetic resonance image enhancer, the chelate-metal complex may be formulated with an excipient, for example, unreacted saccharide, emulsifiers, solvents, such as saline solution, buffers, or the like, may be added by methods well known in the art.

The non-ionic agents of the invention show improved metal-ligand stability, compared to those containing DTPA-bisamide derivatives. This is due to the amide group being replaced by the basic amino groups. (Examples 1-7)

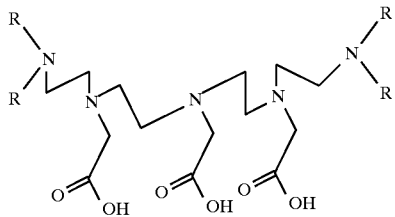

METHODS OF PREPARATION OF CHELATING AGENT

EXAMPLE 1
3,6,9-tris(carboxymethyl)-1, 11-bis(dimethylamino)-3, 6,9-triazaundecane.

a) Diethylenetriamine (3.8 ml) was dissolved in 25 ml of water and 4.0 g sodium hydroxide was added. To this the solution of p-toluenesulfonylcholoride (19.1 g) in either (60 ml) was added dropwise over an hour with vigorous. stirring. The mixture was stirred for an additional two hours. The white precipitate was filtered, washed with ether and water, and recrystallized with methanol.

b) 9.8 g 2-dimethylaminoethylchloride hydrochloride was dissolved in 200 ml of anhydrous N,N-Dimethylformamide (hereinafter "DMF") and 13 g cesium carbonate was added under nitrogen. Then 11.3 g of the product from step (a) dissolved in 100 ml of anhydrous DMF was added dropwise over the period of four hours, with constant stirring. The mixture was stirred overnight at room temperature. Then the mixture was heated at 75° C. for 48 hours. The solvent was removed by evaporation under reduced pressure. The residue was mixed with 200 ml of water, filtered, and washed with methanol.

c) 12.7 g of the product from step (b) was added to 150 ml of 98% sulfuric acid and the mixture was stirred at 1000 C for 70 hours. It was then cooled in ice and 500 ml of ether was slowly added. The precipitate was filtered and washed with ether. The salt was then stirred in 100 ml of water. 1 g of activated carbon was added, and then heated to 80° C. and the solution was filtered hot. To the filtrate, 1.0 M barium chloride was added until no more precipate formed with addition of barium chloride. The precipitate was filtered out and the filtrate was evaporated to dryness under reduced pressure.

d) 4.16 g of bromoacetic acid and 1.2 g of sodium hydroxide were dissolved in 10 ml of water. This was added to a solution of 5.30 g product from step (c) and 2 g sodium hydroxide in 5 ml of water, while stirring. The mixture was heated at 85° C. for four hours. pH was maintained at 8–10. The mixture was cooled and pH adjusted to 3.0 with concentrated hydrobromic acid. 25 ml of ethanol was added, and the solution was stirred for 1.5 hours in an ice bath. The white precipitate formed was filtered and washed with ethanol.

EXAMPLE 2
3,6,9-tris(carboxymethyl)-1,11-bis(N-methylglucamino)-3, 6,9-triazaundecane.

a) 5.67 g of sodium borohydride was added to 100 ml of DMF and then 10.7 g of DTPA-bisanhydride was added while stirring. The mixture was stirred at room temperature for 7 hours after which acetic acid was slowly added to destroy the excess sodium borohydride. The residue was stirred with water and filtered. The filtrate was evaporated to dryness under reduced pressure and washed with ethanol.

200 ml of methanol was added, to which 10 ml concentrated sulfuric acid was added. The reaction mixture was refluxed for 4 hours, and the solvent was evaporated to dryness. The ester was dissolved in CHCl$_3$ and washed with a saturated solution of sodium carbonate. The organic layer was dried over potassium carbonate and evaporated to dryness.

b) 7.4 g of the product from step (a) was taken in 50 ml of dichloromethane and 5.6 ml of triethylamine was added. Then the solution was prepared by dissolving 7.6 g of p-toluenesulfonylchloride in 50 ml dichloromethane was added dropwise over an hour. The reaction mixture was stirred for an additional 6 hours, washed with water, dried over potassium carbonate and evaporated to dryness.

c) 10 g of the di-tosylate from step (b) was dissolved in 50 ml of anhydrous DMF, which was added dropwise to the solution of N-Methylglucamine (5.9 g) in 30 ml of anhydrous DMF containing 9.75 g of cesium carbonate, over the period of 4 hours. The mixture was stirred overnight at room temperature and then heated at 70°–80° C. for 48 hours. This reaction was carried out under nitrogen atmosphere. Then the solvent was removed by evaporation under reduced pressure and washed with water.

d) 6.3 g of the product from step (c) was taken in 100 ml of 6M hydrochloric acid and refluxed for 48 hours. After cooling, the solution was washed with chloroform and evaporated to dryness under reduced pressure.

EXAMPLE 3
3,6,9-tris(carboxymethyl)-1,11-bis(diethanolamino)-3,6,9-triazaundecane a) 5.67 g of sodium borohydride was added to 100 ml of DMF and then 10.7 g of DTPA-bisanhydride was added while stirring. The mixture was stirred at room temperature for 7 hours after which acetic acid was slowly added to destroy the excess sodium brohydride. The residue was stirred with water and filtered. The filtrate was evaporated to dryness under reduced pressure and washed with ethanol.

200 ml of methanol was added, to which 10 ml concentrated sulfuric acid was added. The reaction mixture was refluxed for 4 hours, and the solvent was evaporated to dryness. The ester was dissolved in CHCl$_3$ and washed with a saturated solution of sodium carbonate. The organic layer was dried over potassium carbonate and evaporated to dryness.

b) 7.4 g of the product from step (a) was taken in 50 ml of dichloromethane and 5.6 ml of triethylamine was added. Then the solution was prepared by dissolving 7.6 g of p-toluenesulfonylchloride in 50 ml dichloromethane was added dropwise over an hour. The reaction mixture was stirred for an additional 6 hours, washed with water, dried over potassium carbonate and evaporated to dryness.

c) 10 g of the di-tosylate from step (b) was dissolved in 50 ml of anhydrous DMF, which was added dropwise to the solution of diethanolamine (3.1 g) in 30 ml of anhydrous DMF containing 9.75 g of cesium carbonate, over the period of 4 hours. The mixture was stirred overnight at room temperature and then heated at 70°–80° C. for 48 hours. This reaction was carried out under nitrogen atmosphere. Then the solvent was removed by evaporation under reduced pressure and washed with water.

d) 6.2 g of the product from step (c) was taken in 100 ml of 6M hydrochloric acid and refluxed for 48 hours. The solution was cooled and washed with chloroform and evaporated to dryness under reduced pressure and washed with ethanol.

EXAMPLE 4

3,6,9-tris(carboxymethyl)-1,11-bis(tris(hydroxymethyl) aminomethane)-3,6,9-triazaundecane.

a) 5.67 g of sodium borohydride was added to 100 ml of DMF and then 10.7 g of DTPA-bisanhydride was added while stirring. The mixture was stirred at room temperature for 7 hours after which acetic acid was slowly added to destroy the excess sodium brohydride. The residue was stirred with water and filtered. The filtrate was evaporated to dryness under reduced pressure and washed with ethanol.

200 ml of methanol was added, to which 10 ml concentrated sulfuric acid was added. The reaction mixture was refluxed for 4 hours, and the solvent was evaporated to dryness. The ester was dissolved in $CHCl_3$ and washed with a saturated solution of sodium carbonate. The organic layer was dried over potassium carbonate and evaporated to dryness.

b) 7.4 g of the product from step (a) was taken in 50 ml of dichloromethane and 5.6 ml of triethylamine was added. Then the solution was prepared by dissolving 7.6 g of p-toluenesulfonylchloride in 50 ml dichloromethane was added dropwise over an hour. The reaction mixture was stirred for an additional 6 hours, washed with water, dried over potassium carbonate and evaporated to dryness.

c) 10 g of the di-tosylate from step (b) was dissolved in 50 ml of anhydrous DMF, which was added dropwise to the solution of tri(hydroxymethyl)amino methane (5.1 g) in 30 ml of anhydrous DMF containing 9.75 g of cesium carbonate, over the period of 48 hours. The mixture was stirred overnight at room temperature and then heated at 80° C. for 4 hours. The reaction was carried out under nitrogen atmosphere. Then the solvent was removed by evaporation under reduced pressure and washed with water.

d) 7.5 g of the product from step (c) was taken in 100 ml of 6M hydrochloric acid and refluxed for 48 hours. After cooling, the solution was washed with chloroform and evaporated to dryness under reduced pressure and washed with methanol.

EXAMPLE 5

3,6,9-tris(carboxymethyl)-1,11-bis(glucosamino)-3,6,9-triazaundecane.

a) 5.67 g of sodium borohydride was added to 100 ml of DMF and then 10.7 g of DTPA-bisanhydride was added while stirring. The mixture was stirred at room temperature for 7 hours after which acetic acid was slowly added to destroy the excess sodium brohydride. The residue was stirred with water and filtered. The filtrate was evaporated to dryness under reduced pressure and washed with ethanol.

200 ml of methanol was added, to which 10 ml concentrated sulfuric acid was added. The reaction mixture was refluxed for 4 hours, and the solvent was evaporated to dryness. The ester was dissolved in $CHCl_3$ and washed with a saturated solution of sodium carbonate. The organic layer was dried over potassium carbonate and evaporated to dryness.

b) 7.4 g of the product from step (a) was taken in 50 ml of dichloromethane and 5.6 ml of triethylamine was added. Then the solution was prepared by dissolving 7.6 g of p-toluenesulfonylchloride in 50 ml dichloromethane was added dropwise over an hour. The reaction mixture was stirred for an additional 6 hours, washed with water, dried over potassium carbonate and evaporated to dryness.

c) 10 g of the di-tosylate from step (b) was dissolved in 50 ml of anhydrous DMF. This was added dropwise to the mixture of 6.4 g of glucosamine hydrochloride, 4.2 ml of triethylamine, and 9.75 g of cesium carbonate over the period of 4 hours. The mixture was stirred overnight at room temperature and then heated at 65° C. for 48 hours. This reaction was carried out under nitrogen atmosphere. Then the solvent was removed by evaporation under reduced pressure and washed with water and methanol.

d) 7.7 g of the product from step (c) was taken in 100 ml of 6M hydrochloric acid and refluxed for 48 hours. The solution was cooled, evaporated to dryness under reduced pressure and washed with methanol.

EXAMPLE 6

3,6,9-tris (carboxymethyl)-1, 11-bis (galactosamino)-3, 6,9-triazaundecane.

a) 5.67 g of sodium borohydride was added to 100 ml of DMF and then 10.7 g of DTPA-bisanhydride was added while stirring. The mixture was stirred at room temperature for 7 hours after which acetic acid was slowly added to destroy the excess sodium brohydride. The residue was stirred with water and filtered. The filtrate was evaporated to dryness under reduced pressure and washed with ethanol.

200 ml of methanol was added, to which 10 ml concentrated sulfuric acid was added. The reaction mixture was refluxed for 4 hours, and the solvent was evaporated to dryness. The ester was dissolved in $CHCl_3$ and washed with a saturated solution of sodium carbonate. The organic layer was dried over potassium carbonate and evaporated to dryness.

b) 7.4 g of the product from step (a) was taken in 50 ml of dichloromethane and 5.6 ml of triethylamine was added. Then the solution was prepared by dissolving 7.6 g of p-toluenesulfonylchloride in 50 ml dichloromethane was added dropwise over an hour. The reaction mixture was stirred for an additional 6 hours, washed with water, dried over potassium carbonate and evaporated to dryness.

c) 10 g of the di-tosylate from step (b) was dissolved in 50 ml of anhydrous DMF, which was added dropwise to the mixture containing 6.4 g of galactosamine hydrochloride, 4.2 ml of triethylamine and 9.75 g of cesium carbonate in 100 ml anhydrous DMF, over the period of 4 hours. The mixture was stirred overnight at room temperature and then heated at 65° C. for 48 hours. This reaction was carried out under nitrogen. The solvent was evaporated under reduced pressure and the residue was washed with cold water and methanol.

d) 7.7 g of the product from step (c) was taken in 100 ml of 6M hydrochloric acid and refluxed for 48 hours. The solution was cooled, evaporated to dryness under reduced pressure and washed with methanol.

EXAMPLE 7

3,6,9-tris (carboxymethyl)-1, 11-bis (3,4-dihydroxybenzylamino)-3,6,9-triazaundecane.

a) 5.67 g of sodium borohydride was added to 100 ml of DMF and then 10.7 g of DTPA-bisanhydride was added while stirring. The mixture was stirred at room temperature for 7 hours after which acetic acid was slowly added to destroy the excess sodium brohydride. The residue was stirred with water and filtered. The filtrate was evaporated to dryness under reduced pressure and washed with ethanol.

200 ml of methanol was added, to which 10 ml concentrated sulfuric acid was added. The reaction mixture was refluxed for 4 hours, and the solvent was evaporated to dryness. The ester was dissolved in $CHCl_3$ and washed with a saturated solution of sodium carbonate. The organic layer was dried over potassium carbonate and evaporated to dryness.

b) 7.4 g of the product from step (a) was taken in 50 ml of dichloromethane and 5.6 ml of triethylamine was added. Then the solution was prepared by dissolving 7.6 g of p-toluenesulfonylchloride in 50 ml dichloromethane was added dropwise over an hour. The reaction mixture was stirred for an additional 6 hours, washed with water, dried over potassium carbonate and evaporated to dryness.

c) 10 g of the di-tosylate from step (b) was dissolved in 50 ml of anhydrous DMF. This was added dropwise to the mixture containing 6.6 g of 3,4-dihydroxybenzylamine hydrobromide, 4.2 ml triethylamine and 9.25 g cesium carbonate in 100 ml of anhydrous DMF over the period of 4 hours, under nitrogen. The mixture was stirred at room temperature overnight and then heated to 80° C. for 48 hours. The solvent was evaporated under reduced pressure and the residue was washed with water and chloroform.

d) 6.9 g of the product from step (c) was taken in 100 ml of hydrochloric acid and refluxed for 48 hours. The solution was cooled, evaporated to dryness under reduced pressure and washed with methanol.

EXAMPLE 8

3,6,-bis(carboxymethyl)-1,8-bis(N-carboxymethylglucosamino)-3,6-diazaoctane a) 5.92 g of N,N'-bis(2-hydroxyethyl) ethylenediamine was dissolved in 150 ml of ethanol. To this 13.5 g of ethylbromoacetate and 13 g of cesium carbonate were added. The mixture was refluxed for 18 hours, cooled, filtered, and evaporated under reduced pressure. The residue was taken in 500 ml of dichloromethane, washed with water, dried over potassium carbonate, and evaporated to dryness.

b) 6.6 g of the product from step (a) was taken in 100 ml of dichloromethane and 4.2 ml of triethylamine was added. To this solution of p-toluenesulfonylchloride (5.7 g) in dichloromethane (20 ml) was added dropwise over an hour. The mixture was allowed to stir for an additional 4 hours, washed with water, dried over $K_2CO_3$. Then it was evaporated to dryness and washed with methanol.

c) 7.4 g of the product step (b) was dissolved in 75 ml anhydrous DMF. This was added dropwise to the mixture containing 8.6 g glucosamine hydrochloride, 5.6 ml of triethylamine and 13 g of cesium carbonate in 100 ml of anhydrous DMF, over the period of 4 hours under nitrogen. The mixture was stirred overnight at room temperature and then heated to 65° C. for 48 hours. Then the solvent was evaporated to dryness under reduced pressure. The residue was washed with ice cold water and ethanol.

d) 9.6 g of the product from step (c) was taken in 100 ml of ethanol and 5.0 g ethylbromoacetate, and 9.25 g of cerium carbonate were added. The mixture was heated at 70° C. for 18 hours, cooled, filtered, and evaporated under reduced pressure. The residue was washed with ether.

e) 8.0 g of the product from step (d) was taken in 100 ml of 6M hydrochloric acid and refluxed for 48 hours. After cooling, the solution was evaporated to dryness under reduced pressure. The residue was washed with methanol and dried in vacuum.

EXAMPLE 9

3,6,-bis(carboxymethyl)-1,8-bis(N-carboxymethylgalactosamino)-3,6-diazaoctane a) 5.92 g of N,N'-bis(2-hydroxyethyl) ethylenediamine was dissolved in 150 ml of ethanol. To this 13.5 g of ethylbromoacetate and 13 g of cesium carbonate were added. The mixture was refluxed for 18 hours, cooled, filtered, and evaporated under reduced pressure. The residue was taken in 500 ml of dichloromethane, washed with water, dried over potassium carbonate, and evaporated to dryness.

b) 6.6 g of the product from step (a) was taken in 100 ml of dichloromethane and 4.2 ml of triethylamine was added. To this solution of p-toluenesulfonylchloride (5.7 g) in dichloromethane (20 ml) was added dropwise over an hour. The mixture was allowed to stir for an additional 4 hours, washed with water, dried over $K_2CO_3$. Then it was evaporated to dryness and washed with methanol.

c) 7.4 g of the product step (b) was dissolved in 75 ml anhydrous DMF. This was added dropwise to the mixture containing 8.6 g galactosamine hydrochloride, 5.6 ml of triethylamine and 13 g of cesium carbonate in 100 ml of anhydrous DMF, over the period of 4 hours under nitrogen. The mixture was stirred overnight at room temperature and then heated to 65° C. for 5 hours. Then the solvent was evaporated to dryness under reduced pressure. The residue was washed with ice cold water and ethanol.

d) 9.6 g of the product from step (c) was taken in 100 ml of ethanol and 5.0 g ethylbromoacetate, and 9.25 g of cerium carbonate were added. The mixture was heated at 70° C. for 18 hours, cooled, filtered, and evaporated under reduced pressure. The residue was washed with ether.

e) 8.0 g of the product from step (d) was taken in 100 ml of 6M hydrochloric acid and refluxed for 48 hours. After cooling, the solution was evaporated to dryness under reduced pressure. The residue was washed with methanol and dried in vacuum.

EXAMPLE 10

DTPA-bis(glucosamide)

8.6 g of glucosamine hydrochloride was dissolved in 150 ml of anhydrous DMSO and 5.6 ml of triethylamine was added. The mixture was stirred for 15 minutes. Then 7.1 g DTPA bisanhydride was added in small portions, with constant stirring. After stirring for 2 hours at room temperature, the temperature was raised to 50° C. for 10 minutes. It was allowed to cool and was filtered. The bisamide was precipitated by adding 500 ml of isopropylalcohol. The product was filtered with scintered glass funnel, washed with ether. The product was dissolved in 25 ml water and stirred for 10 minutes with 1 g of activated charcoal and filtered. 250 ml of ethanol was added and the precipitate was filtered and washed with ether.

EXAMPLE 11

DTPA-bis(galactosamide)

8.6 g of galactosamine hydrochloride was dissolved in 150 ml of anhydrous DMSO. 5.6 ml of triethylamine was added and stirred for 15 minutes. The 7.1 g DTPA bisanhydride was added slowly in small portions, with constant stirring. The mixture was stirred at room temperature for 2 hours, and then the temperature was raised to 50° C. for 10 minutes. It was allowed to cool and filtered. 500 ml of isopropylalcohol was added and the bisamide was filtered. The product was dissolved in 20 ml of water and 1 g of activated charcoal was added, stirred, and filtered. The final product was precipitated with 250 ml of ethanol, filtered and washed with ethanol and ether.

EXAMPLE 12

DTPA-bis(pyridoxamide)

4.8 g of pyridoxamine dihydrochloride was dissolved in 75 ml of anhydrous DMSO and 5.6 ml of triethylamine was added. The mixture was stirred for 15 minutes; then 3.5 g DTPA bisanhydride was added in small portions, with constant stirring. After stirring overnight at room temperature, the mixture was heated at about 60° C. for one hour. It was allowed to cool and was then filtered. 300 ml of 2:1 mixture of isopropyl alcohol and ether was added and the bisamide was filtered. The product was dissolved in water and passed through an amberlite CG-400 acetate anion exchange column. The column was washed with water and the product was eluted with 1M acetic acid. The DTPA-bispyridoxamide (DTPA-BPA) was obtained by evaporating the solution under reduced pressure.

EXAMPLE 13

Poly-(DTPA-ethylenediamide)

7.1 g of DTPA bisanhydride was taken in 150 ml of anhydrous DMF and 14 ml of triethylamine was added. Then 2.2 ml ethylenediamine dissolved 50 ml of anhydrous DMF was added slowly. With constant vigorous stirring under nitrogen, the mixture was stirred at room temperature for 30 minutes, then at 50° C. for 3 hours. The mixture was stirred overnight. Solvent was removed by evaporation under reduced pressure at 60° C. The residue was dissolved in water and dialyzed in water for 48 hours. Then the product was isolated by precipitation with ethanol, and dried in a vacuum.

EXAMPLE 14

DTPA-ethylenediamine-methacrylate copolymer a) 10.7 g DTPA bisanhydride was added slowly with stirring to 100 ml of ethylenediamine. The mixture was heated at 60° C. for 1 hour and was stirred at room temperature for an additional 3 hours. Ethylenediamine was removed by evaporation under reduced pressure; it was then recrystallized from water-ethanol.

b) The diamide of DTPA (8.3 g) from step (a) was taken in 150 ml of anhydrous DMF and 10 ml of pyridine was added. Then 2.1 ml of methylmethacrylate was added and stirred overnight. The methanol produced in the reaction was removed by reflux.

50 mg of benzoylperoxide was added and the mixture was stirred at room temperature for 30 minutes under nitrogen. Then it was heated to 80° C. for 5 hours. Cooled, the solvent was removed by evaporation under reduced pressure. The product was taken into water and dialyzed for 48 hours and isolated.

COMBINATION OF CHELATING AGENT WITH METAL IONS

EXAMPLE 15

Gadolinium (III) Chelates

Gadolinium (III) chloride was mixed with an equimolar quantity of ligand (Examples 1–12) in water. In the case of Gd(III) polymer (Examples 13–14) complexes, gadolinium (III) chloride was added in equimolar quantity to the DTPA content. The mixture was heated to 65° C. for two hours at pH 5.8. The reaction was monitored by testing for free gadolinium. The solvent was removed by evaporation to dryness under reduced pressure. The residue was washed with ethanol and ether. Similarly, by substituting dysprosium chloride, iron chloride, chromium chloride, manganese chloride, cobalt chloride, or technetium pertechnetate in the presence of stannous ion for gadolinium chloride one can obtain the respective metal chelates.

MAGNETIC RESONANCE CONTRAST ENHANCEMENT EXPERIMENTS

New Zealand White rabbits were used for all magnetic resonance imaging (MRI) experiments. A General Electric 1.5 Tesla system was used with the knee coil. T1W spin echo images were obtained every 10 minutes following contrast injection. Data points were takes as the time at the end of the scan. Each data point was measured in triplicate with sample signal intensities taken from the liver, kidney, and muscle. TR=750 msec. TE=37 msec. NEX=4. Flow compensation was used. Sedation was performed by using an initial injection of intramuscular ketamine at 110 mg/kg and pentobarbital intravenously at 2.2 cc/kg. Sedation was maintained with intermittent pentobarbital injections as needed at 1 cc/kg.

EXAMPLE 16

Two rabbits were given gadolinium DTPA bis-glucosamide at 0.1 mM/kg intravenously. MR images were taken before and after the injection of the contrast agent. The contrast enhancement of liver and kidneys was well demonstrated at 11 minutes after contrast injections. The maximum contrast enhancement was maintained until 22 minutes and then decreased gradually. The decrease in contrast was slower in the liver than in the kidney. This contrast agent showed improved enhancement of the liver and kidney compared to Gd DTPA.

EXAMPLE 17

The gadolinium DTPA galactosamide was given intravenously at 0.1 mM/kg. MR images were taken before and after the injection of contrast agent. The contrast enhancement of liver and kidney was well demonstrated at 11 minutes. The maximum contrast enhancement in kidneys was observed at 22 minutes and then decreased very slowly. In the case of liver, the maximum contrast enhancement was observed at 11 minutes and then decreased rapidly. The contrast agent appears to have been cleared from the liver at 76 minutes. This contrast agent exhibited improved enhancement of the liver compared to Gd DTPA.

EXAMPLE 18

Gadolinium DTPA bis-pyriodoxamide was given intravenously at 0.1 mM/kg. MR images were taken before and after the injection of contrast agent. The contrast enhancement of the kidney was well demonstrated and maximum at 11 minutes. The animal suffered anesthetic overdose and the experiment was not continued past 31 minutes. This agent exhibited improved renal enhancement compared to Gd DTPA. It gave negative liver enhancement. Perhaps the dosage was took high; if it is highly selective for the liver, negative enhancement can occur secondary to T2 dephasing effects.

We claim:

1. A contrast enhancing agent comprising a chelating agent represented by the formula:

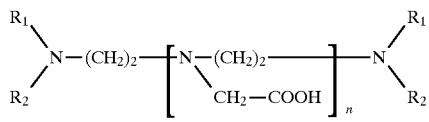

wherein n=an integer between 1 and 3; and $R_1$ and $R_2$ are the same or different, independently, and are selected from the group consisting of H, Alkyl ($C_{1-18}$), aryl, arylalkyl, mono and polyhydroxyaryl, mono and polymethoxyaryl, substituted aryl, substituted hydroxyaryl, alkoxyalkyl, arylalkoxyalkyl, cyclohexyl, mono or polyhydroxy cyclohexyl, furfuryl, pyranylalkyl, tetrahydropyranylalkyl, and monosaccharide, and wherein at least one of $R_1$ or $R_2$ is a monosaccharide.

2. A composition of matter comprising the chelating agent of claim 1, and a metal ion having at least one unpaired electron chelated to said chelating agent.

3. The compounds of claim 2, wherein said metal ion is selected from the lanthanide group of metals.

4. The compounds of claim 2, wherein said metal ion is Gadolinium.

5. The compounds of claim 2, wherein said metal ion is selected from the group consisting of Chromium, Manganese, Iron, Cobalt, and Technetium.

6. A composition of matter comprising the chelating agent and metal ions of claim 2, and an excipient for administration to a patient for magnetic resonance tomography.

7. A method for using the composition matter of claim 3 for imaging a patient, comprising the steps of:

administering the compound to a patient; and taking images of the patient.

8. A magnetic resonance contrast enhancing agent comprising a chelating agent represented by the formula A:

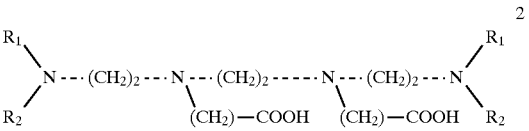

wherein $R_1$ and $R_2$ are the same or different, independently, and are selected from the group consisting of H, Alkyl ($C_{1-18}$), monohydroxy or polyhydroxy alkyl ($C_{1-18}$), aryl, arylalkyl, mono or polyhydroxyaryl, substituted aryl or substituted hydroxyaryl, alkoxyalkyl, arylalkoxyalkyl, cyclohexyl, mono or polyhydroxy cyclohexyl, furfuryl, tetrahydrofurfuryl, pyranylalkyl, tetrahydropyranylalkyl, and monosaccharide, and wherein at least one of $R_1$ and $R_2$ is a monosaccharide.

9. A magnetic resonance contrast enhancing agent comprising a chelating agent represented by the formula A:

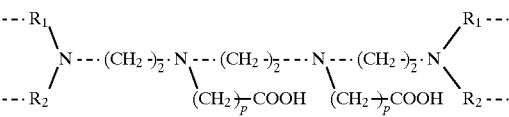

wherein $R_2$ is —$CH_2$—COOH, and $R_1$ is a monosaccharide.

10. A magnetic resonance contrast enhancing agent comprising a chelating agent represented by the formula A:

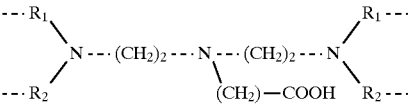

wherein $R_2$ is —$CH_2$—COOH, and $R_1$ is —$CH_2$—CO—NH—$R_3$;

wherein —NH—$R_3$ is selected from the group consisting of glucosamine, galactosamine, and any amino sugar.

* * * * *